US00PP09308P

United States Patent [19]

Meilland

[11] Patent Number: Plant 9,308

[45] Date of Patent: Oct. 3, 1995

[54] HYBRID TEA ROSE PLANT NAMED 'MEIBIGOUD'

[75] Inventor: Alain A. Meilland, Antibes, France

[73] Assignee: The Conard-Pyle Company, West Grove, Pa.

[21] Appl. No.: 356,621

[22] Filed: Dec. 15, 1994

[51] Int. Cl.[6] ..... A01H 5/00

[52] U.S. Cl. ..... Plt./20

[58] Field of Search ..... Plt./20, 21

[56] References Cited

U.S. PATENT DOCUMENTS

| | | | |
|---|---|---|---|
| P.P. 3,452 | 1/1974 | Meilland | Plt./20 |
| P.P. 4,037 | 4/1977 | Paolino | Plt./20 |
| P.P. 6,171 | 5/1988 | Meilland | Plt./20 |
| P.P. 7,510 | 4/1991 | Kordes | Plt./20 |
| P.P. 8,507 | 12/1993 | Meilland | Plt./20 |

*Primary Examiner*—Howard J. Locker
*Attorney, Agent, or Firm*—Burns, Doane, Swecker & Mathis

[57] ABSTRACT

A new and distinct variety of Hybrid Tea rose plant is provided which abundantly and continuously forms attractive long-lasting double bright red blossoms. Such blossoms are borne on long erect stems and commonly open slowly and completely when cut and placed in a vase. The plant exhibits attractive wide dark green semi-glossy foliage, and is well suited for use in the production of cut flowers under greenhouse growing conditions. Additionally, the plant exhibits good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired charactertistics. The female parent (i.e., the seed parent) of the new variety was the product of the cross of the Meired variety (U.S. Plant Pat. No. 3,452) by the product of the cross of the Meirodium variety (U.S. Plant Pat. No. 4,037 and the Meidiaplou variety (U.S. Plant Pat. No. 7,624). The Meired variety sometimes is known as the Visa variety. The male parent (i.e., the pollen parent) was the product of the pollination of the Dallas variety (non-patented in the United States) and the First Red variety (non-patented in the United States). The parentage of the new variety can be summarized as follows:

[Meired×(Meirodium×Meidiaplou)]×(Dallas ×First Red).

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance long-lasting double bright red blossoms on long erect stems that commonly open slowly and completely when cut and placed in a vase, (b) forms attractive wide dark green foliage that contrasts well with the blossom coloration, and (c) is particularly well suited for cut flower production.

The new variety well meets the needs of the horticultural industry and can be grown to advantage when producing cut flowers under greenhouse conditions.

The new variety has been found to undergo asexual propagation in France by a number of routes, including budding, grafting, and cuttage. The characteristics of the new variety have been found by such methods in France to be stable and to be strictly transmissible from one generaton to another.

The new variety has been named the Meibigoud variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa indica* understock and growing in greenhouse at Le Cannet des Maures, Var, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

Figures 1, 2, 3, 4, 5, 6, 7, 8, 9, 10, 11, 12, 13, 14, 15, 16:
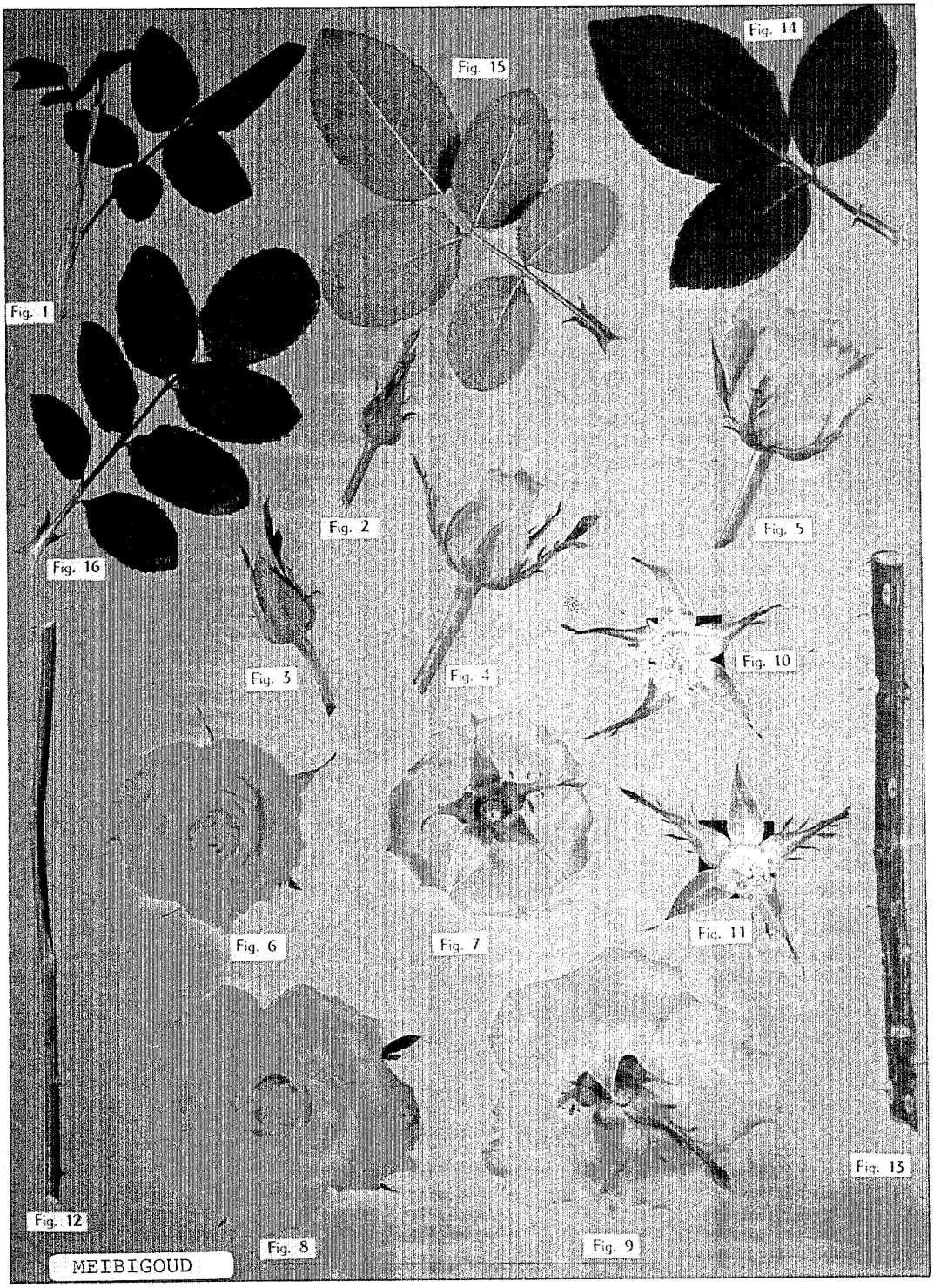

The chart used in the identification of the colors is that of The Royal Horticultural Society (R.H.S. Colour Chart). The description is based on the observation of two year-old plants while budded on *Rosa indica* understock and growing during September in greenhouses at Le Cannet des Maures, Var, France. The coloration in common terms precedes reference to the chart.

Class: Hybrid Tea.

Plant:

*Height.*—Approximately 70 to 90 cm. on average at the end of the growing season.

*Habit.*—Erect.

Branches:

*Color.*—Young stems: medium green, Green Group 143A. Adult wood: medium green, Yellow-Green Group 147A.

*Thorns.*—Size: small. Quantity: moderately numerous. Color: greenish.

Leaves:

*Stipules.*—Adnate, pectinate, very wide and linear.

*Petioles.*—Upper surface: striped reddish brown on young foliage, medium green on adult foliage, and more or less glandular. Under surface: light green and generally smooth.

*Leaflets.*—Number: 3, 5 (most often), and 7. Shape: as illustrated. Serration: simple and regular. Texture: very consistent. General appearance: dense and semi-glossy foliage. Color (young foliage): upper surface: dark green, Green Group 139A, and more or less tinted with reddish coloration. under surface: dark green, Green Group 139A, and more or less tinted with reddish coloration. Color (adult foliage): upper surface: dark green, Green Group 139A. under surface: medium green, Green Group 137C.

Inflorescence:

*Number of flowers.*—Usually one flower per stem.

*peduncle.*—Light green in coloration. The length commonly is approximately 7 to 8 cm. on average.

*Sepals.*—Upper surface: tomentose, and greenish in coloration. Under surface: medium green, and commonly have more or less glandular and appendiculated edges.

*Buds.*—Shape: conical. Length: approximately 4 cm. on average. Size: medium. Color upon opening: upper surface: Post Office Red, Red Group 45B, and widely suffused with bright Vermilion Red, Red Group 44A. under surface: Guardsman Red, Red Group 45B.

*Flower.*—Shape: cup-shaped. Diameter: approximately 11 to 12 cm. on average. Color (when opening begins): upper surface: Post Office Red, Red Group 45B, and widely suffused with Vermilion Red, Red Group 44B. under surface: Strawberry Red, Red Group 46B. Color (when blooming): upper surface: Post Office Red, Red Group 45B, and widely suffused with light Vermilion Red, Red Group 44C. under surface: Cherry Red, Red Group 45C. Color (at end of opening): upper surface: Post Office Red, Red Group 45B, and widely suffused with Vermilion Red, Red Group 44B. under surface: Cherry Red, Red Group 45C, and widely suffused with light Cardinal Pink, Red Group 53D. Fragrance: none. Lasting quality: long when cut and placed in a vase. Petal number: approximately 35 on average. Petal shape: rounded. Petal drop: good. Stamen number: approximately 122 on average. Anthers: normal, ochre in coloration and tend to be disposed under the stigmas. Filaments: light yellow in coloration. Pistils: approximately 92 on average. Stigmas: strawlike in coloration. Styles: dark fuchsia in coloration, tomentose at the base, and commonly twisted and joined together. Receptacle: medium green, smooth, and in longitudinal section in the shape of a tube.

Development:

*Vegetation.*—Strong.

*Blooming.*—Abundant.

*Aptitude to bear fruits.*—Good.

*Resistance to diseases.*—Good.

I claim:

1. A new and distinct variety of Hybrid Tea rose plant characterized by the following combination of characteristics:

(a) forms in abundance long-lasting double bright red blossoms on long erect stems that commonly open slowly and completely when cut and placed in a vase, (b) forms attractive wide dark green foliage that contrasts well with the blossom coloration, and (c) is particularly well suited for cut flower production; substantially as herein shown and described.

* * * * *

MEIBIGOUD